United States Patent
Dalicsek et al.

(10) Patent No.: US 9,056,314 B2
(45) Date of Patent: *Jun. 16, 2015

(54) PALLADIUM CATALYST, METHOD FOR ITS PREPARATION AND ITS USE

(71) Applicants: H4SEP KFT, Budapest (HU); CHINOIN GYÓGYSZER-ÉS VEGYÉSZETI TER-MÉKEK GYÁRA ZRT, Budapest (HU)

(72) Inventors: Zoltán Dalicsek, Mezökovácsháza (HU); Tibor Soós, Budapest (HU); Zoltán Finta, Budapest (HU); Géza Timári, Vecsés (HU); Gábor Vlád, Budapest (HU)

(73) Assignees: H4SEP KFT, Budapest (HU); CHINOIN GYOGYSZER-ES VEGYESZETI TER-MEKEK GYARA ZRT, Budapest (HU)

( * ) Notice: Subject to any disclaimer, the term of this patent is extended or adjusted under 35 U.S.C. 154(b) by 0 days.

This patent is subject to a terminal disclaimer.

(21) Appl. No.: 13/918,735

(22) Filed: Jun. 14, 2013

(65) Prior Publication Data

US 2013/0281700 A1 Oct. 24, 2013

Related U.S. Application Data

(63) Continuation-in-part of application No. PCT/HU2011/000122, filed on Dec. 13, 2011.

(51) Int. Cl.

| C07F 15/00 | (2006.01) |
|---|---|
| C09K 3/00 | (2006.01) |
| B01J 31/24 | (2006.01) |
| C07B 35/02 | (2006.01) |
| C07B 37/04 | (2006.01) |
| C07C 15/52 | (2006.01) |
| C07C 15/54 | (2006.01) |
| C07C 41/30 | (2006.01) |
| C07C 201/12 | (2006.01) |
| C07C 205/06 | (2006.01) |
| C07D 213/30 | (2006.01) |
| C07D 217/02 | (2006.01) |
| C07D 217/16 | (2006.01) |
| C07C 2/88 | (2006.01) |
| C07C 17/26 | (2006.01) |
| C07D 209/08 | (2006.01) |

(Continued)

(52) U.S. Cl.

CPC .......... *B01J 31/2404* (2013.01); *B01J 31/2447* (2013.01); *C07B 35/02* (2013.01); *C07B 37/04* (2013.01); *C07C 15/52* (2013.01); *C07C 15/54* (2013.01); *C07C 41/30* (2013.01); *C07C 201/12* (2013.01); *C07C 205/06* (2013.01); *C07D 213/30* (2013.01); *C07D 217/02* (2013.01); *C07D 217/16* (2013.01); *B01J 31/2409* (2013.01); *C07C 2/88* (2013.01); *C07C 17/26* (2013.01); *C07D 209/08* (2013.01); *C07D 213/127* (2013.01); *C07D 217/18* (2013.01); *C07D 217/20* (2013.01); *C07D 295/023* (2013.01); *C07C 2/66* (2013.01); *C07D 213/14* (2013.01); *C07D 213/26* (2013.01); *C07D 215/06* (2013.01); *C07D 215/12* (2013.01); *C07D 215/14* (2013.01)

(58) Field of Classification Search
USPC .......................................... 556/21; 252/182.3
See application file for complete search history.

(56) References Cited

U.S. PATENT DOCUMENTS

| 3,530,187 A | 9/1970 | Shryne |
| 2007/0100145 A1 | 5/2007 | Boussie et al. |

FOREIGN PATENT DOCUMENTS

EP   1270582 A1   1/2003

OTHER PUBLICATIONS

Estorach, C.T. et al.: Hydrocarboxylation of terminal alkenes in supercritical carbon dioxide. Eur. J. Inprg. Chem., vol. 22, pp. 3524-3531, 2008.*

(Continued)

*Primary Examiner* — Charanjit Aulakh
(74) *Attorney, Agent, or Firm* — Ann W. Speckman; Speckman Law Group PLLC

(57) ABSTRACT

The invention relates to palladium(0)-tris{tri-[3,5-bis(trifluoromethyl)-phenyl]-phosphine} complex of formula (I), as well as to its preparation and use.

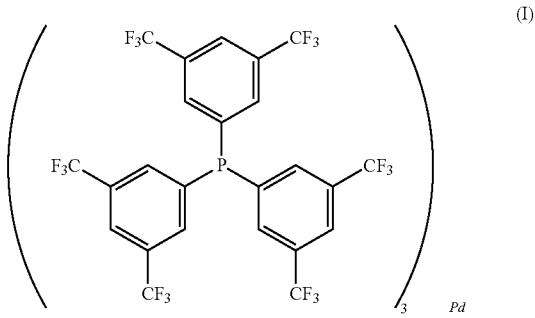

This compound is outstandingly stable, and can be used as catalyst with excellent results.

20 Claims, No Drawings

(51) Int. Cl.
*C07D 213/127* (2006.01)
*C07D 217/18* (2006.01)
*C07D 217/20* (2006.01)
*C07D 295/023* (2006.01)
*C07C 2/66* (2006.01)
*C07D 213/14* (2006.01)
*C07D 213/26* (2006.01)
*C07D 215/06* (2006.01)
*C07D 215/12* (2006.01)
*C07D 215/14* (2006.01)

(56) References Cited

OTHER PUBLICATIONS

Clarke, M.L. et al.: The electron-poor phosphines P{C6H3(CF3)2-3,5}3 and P(C6F5)3 do not mimic phosphites as ligands for hydroformylation. Dalton Transac., vol. 7, pp. 1294-1300, 2005.*

Morita, David K. et al., "Palladium-catalyzed cross-coupling reactions in supercritical carbon dioxide," Chem. Commun., pp. 1397-1938 (Apr. 1998).

Estorach, Clara Tortosa, et al., "Hydrocesterification of 1-alkenes in Supercritical Carbon Dioxide," Catal Lett vol. 122, pp. 76-79 (2008).

\* cited by examiner

PALLADIUM CATALYST, METHOD FOR ITS PREPARATION AND ITS USE

REFERENCE TO RELATED APPLICATIONS

This application is a continuation-in-part of International Patent Application No. PCT/HU2011/000122, filed Dec. 13, 2011, which claims priority to Hungary patent application No. P-1000668, filed Dec. 16, 2010. The disclosures of the related applications are incorporated by reference herein in their entireties.

TECHNICAL FIELD

The invention relates to a new palladium catalyst, more particularly to palladium(0)-tris{tri-[3,5-bis(trifluoromethyl)-phenyl]-phosphine} complex of formula (I)

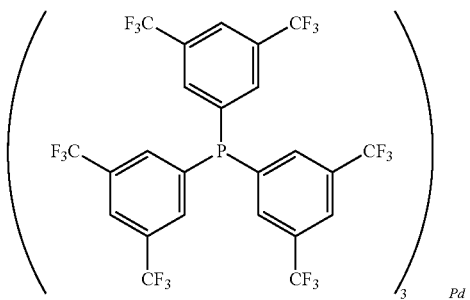

[empirical formula: $Pd\{[3,5-(CF_3)_2-C_6H_3]_3P\}_3$].

The invention relates further to a method for the preparation of the new catalyst. The invention also relates to the use of the new catalyst in reactions requiring such catalysts, more particularly in reactions to form a C—C bond (cross coupling reactions, such as Suzuki, Heck, Stille etc. couplings), in reaction to form a C-heteroatom (C—N, C—O, C—S, C—P, primarily C—N) bond (e.g. Buchwald reaction), and for hydrogenation reactions.

As nowadays cross coupling reactions catalysed by complexes of transition metals (most frequently by Pd and Ni complexes) have an outstanding role in the formation of a C—C bond, and such reactions have brought about radical changes in synthesis routes, the invention will be discussed in the following primarily in connection with cross coupling reactions without, however, restricting its scope to this mode of use.

BACKGROUND

The gross process of cross coupling reactions can be described as

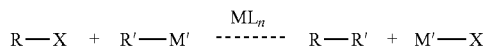

wherein
R and R' represent organic groups to be coupled with a C—C bond,
M is the metal component of the catalyst complex,
L represents the ligands present in the catalyst complex,
n is the number of ligands present,
X is a leaving atom or group (e.g. Cl, Br, I, triflate, mesylate, tosylate), and
M' is a metal or metal-containing group corresponding to the type of the cross coupling reaction concerned (e.g. this metal component is boron for Suzuki-Miyaura coupling, copper for Sonogashira coupling, magnesium for Kharash coupling, silicon for Hiyama coupling, tin for Stille coupling, zinc for Negishi coupling, etc.).

The general mechanism of cross coupling reactions is shown below.

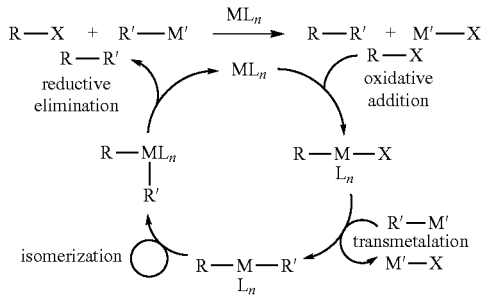

$ML_n$: Pd (O), Ni (O)
X: Cl, Br, I, OTf, $OSO_2R$, SOR, SR, $N_2^+$
M': B = Suzuki-Mayaura coupling, Cu = Sonogashira coupling, Mg = Kharash coupling, Si = Hiyama coupling, Sn = Stille coupling, Zn = Negishi coupling However, from the aspects of practical utilization these methods have some disadvantages, which are particularly pronounced in the field of pharmaceutical industry. One of them is that rather high amounts of catalyst (1-5 mol % related to the substrate) are required, furthermore metal impurities originating from the catalyst can be removed from the end product generally only by tedious and expensive operations. This latter is particularly valid for palladium catalysts, which, in addition, are highly liable to decomposition. As an example, when palladium(0)-tetrakis(tri-phenyl-phosphine) of formula (II),

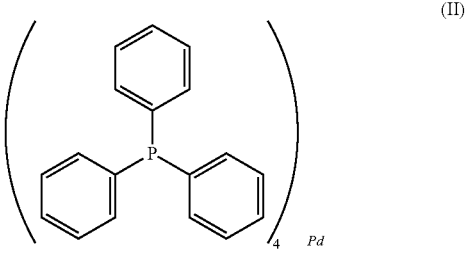

which is still an industrially frequently used catalyst, is stored in air at room temperature, a considerable amount of palladium black separates within a short time, thus it is advisable to store it in a refrigerator under argon atmosphere. Although cross coupling reactions utilizing the catalyst of formula (II) are performed under inert atmosphere, separation of palladium black is still common, which causes not only a considerable loss in catalyst, but tedious time-consuming and expensive purification steps should also be introduced.

DESCRIPTION

The aim of the invention was to provide a new palladium(0) complex catalyst which is much more stable than the palladium(0) complex catalysts used before in cross coupling reactions, and also enables one to considerably reduce the amount of catalyst required for 1 mole of substrate. Within this domain our primary aim was to eliminate palladium black formation, as palladium black formed from Pd(0) complexes is a final state, which catalyst decomposition markedly reduces the overall catalytic efficiency. Additionally, the uncontrolled decomposition of the catalyst often results in intolerable amounts of P being leached into the product.

Now we have found that the palladium(0) complex catalyst of formula (I) fully satisfies the above requirements and has further advantages, too.

Thus, in one aspect, the present invention relates to the palladium(0) complex of formula (I).

This compound is a bright lemon yellow colored solid with outstanding stability: no formation of palladium black could be observed even in samples stored in air at room temperature for more than 20 months.

The compound of formula (I) was stored in air at varying T temperatures and humidities. Samples were taken periodically from the stored product, and the decomposition of the product was examined on the basis of $^{31}P$, $^{19}F$, $^{13}C$ and $^{1}H$ NMR spectra. The results are summarized in the following table.

to determine the metal-ligand binding energies. On B3LYP/lanl2dz level the following measurements were obtained:

|  | L = $P(C_6H_5)_3$ [formula (II)] | L = $P[C_6H_3(CF_3)_2]_3$ [formula (I)] |
|---|---|---|
| PdL → Pd + L | −40.1 kcal/mol | −39.5 kcal/mol |
| $PdL_2$ → PdL + L | −38.0 kcal/mol | −42.3 kcal/mol |
| $PdL_3$ → $PdL_2$ + L | −27.9 kcal/mol | −45.6 kcal/mol |

According to this calculation for compounds comprising three ligands (i.e. of real structures) the metal-ligand binding energy in the compound of formula (I) is about the twofold of that observed for the compound of formula (II). On this basis we assume that the outstanding storage stability of the compound of formula (I) cannot be attributed to a metal-ligand interaction, but to specific ligand-ligand inter-actions(s).

Stability tests were performed on Pd(0)-tris[tri-(substituted phenyl)-phosphine]complex catalysts where two of the three 3,5-(trifluoromethyl)-phenyl groups attached to the phosphorous atom in the ligand were retained, but the third one was replaced by mono-, di- or trimethoxy-phenyl, tri-isopropyl-phenyl or 2-pyridyl group. None of these compounds could even approximate the compound of formula (I)

| Period (month) | T, ° C. | Humidity, % | Colour and grade of decomposition of the stored product |
|---|---|---|---|
| 1 | 5 | Gradually changing | Lemon yellow; no sampling was made |
|  | 25 | 60 | Lemon yellow; no decomposition was shown by NMR |
|  | 30 | 65 | Lemon yellow; no decomposition was shown by NMR |
|  | 40 | 75 | Lemon yellow; no decomposition was shown by NMR |
| 4 | 5 | Gradually changing | Lemon yellow; no sampling was made |
|  | 25 | 60 | Lemon yellow; no decomposition was shown by NMR |
|  | 30 | 65 | Lemon yellow; no decomposition was shown by NMR |
|  | 40 | 75 | Lemon yellow; no decomposition was shown by NMR |
| 7 | 5 | Gradually changing | Lemon yellow; no sampling was made |
|  | 25 | 60 | Lemon yellow; no decomposition was shown by NMR |
|  | 30 | 65 | Lemon yellow; no decomposition was shown by NMR |
|  | 40 | 75 | Lemon yellow; no decomposition was shown by NMR |
| 13 | 5 | Gradually changing | Lemon yellow; no sampling was made |
|  | 25 | 60 | Lemon yellow; no decomposition was shown by NMR |
|  | 30 | 65 | Lemon yellow; no decomposition was shown by NMR |
|  | 40 | 75 | Lemon yellow; no decomposition was shown by NMR |
| 20 | 5 | Gradually changing | Lemon yellow; no sampling was made |
|  | 25 | 60 | Lemon yellow; no decomposition was shown by NMR |
|  | 30 | 65 | Lemon yellow; no decomposition was shown by NMR |
|  | 40 | 75 | Lemon yellow; no decomposition was shown by NMR |

When examining the compound of formula (I) by DSC, decomposition was observed at 169.5° C. in air under atmospheric pressure. When performing the test in inert atmosphere the melting point of the compound was found to be 220° C. Just for the comparison, the non-fluorinated catalyst of formula (II) started to decompose at 98° C.

When examining the possible reasons for the outstanding storage stability of the compound of formula (I) compared to that of its close structural analogue of formula (II), which is widely used in the industry, DFT calculations were performed in storage stability. Thus the outstanding storage stability of the compound of formula (I) is a very surprising characteristic, which does not appear even with its very close structural analogues.

When examining the stability of the catalyst of formula (I) in cross coupling reaction conditions we have found that the catalyst is not sensitive to temperature rise; it retains its stability at any temperature below its melting point. Similarly, an increase in pressure had no influence on the stability of the catalyst.

When examining the stability of the catalyst of formula (I) the following properties have been found:

The catalyst is not soluble in water at industrially relevant temperatures; simultaneously it remains unrestrictedly stable when stored in water.

The solubility of the catalyst in alcohols at room temperature increases with the increase of the carbon atom numbers of the alcohol; however, at the tested temperature intervals of catalytic reactions (110-130° C.) its stability in alcohols decreases in parallel with the increase of the carbon atom numbers of the alcohol. However, the stability of the catalyst can be increased or even completely restored when adding water to the reaction mixture. In aqueous alcohols the dissolution of the catalyst starts at around 90° C. and, depending on the alcohol concerned, it is complete at 110-130° C., where the catalytic activity reaches its maximum. However, even at temperatures leading to complete dissolution no separation of palladium black was observed. Sometimes there occurred a minor tolerable decomposition, which was shown by a slight deepening of the colour of the reaction mixture (from lemon yellow to yellowish brown). It is particularly remarkable that even under such conditions full (100%) conversion could be attained. As a comparison: when the compound of formula (II) was used as catalyst under much milder conditions than those discussed above (atmospheric pressure; boiling point of the reaction mixture) the formation of palladium black could not be avoided, which clearly indicates a considerable decomposition of the catalyst.

In order to avoid the use of superatmospheric pressures, which is undesirable from industrial aspects, the stability of the catalyst of formula (I) was also tested in industrially important polar aprotic and apolar aprotic organic solvents (e.g. dimethyl sulphoxide, dimethyl formamide, ethyl-methyl-ketone, methyl-isobutyl-ketone, N-methyl-pyrrolidine and tetrahydrofuran) in which the catalyst fully dissolves at lower temperatures. No formation of palladium black was observed in these solvents, either, although sometimes the color of the reaction mixture got deeper to some extent during the catalytic reaction (discoloration from lemon yellow to pink, orange, red or brownish were observed). Like with the alcohols discussed above, in some of these solvents the slight stability decrease of the catalyst can be suppressed considerably by adding water to the reaction mixture.

When examining the catalytic activity of the compound of formula (I) in cross coupling reactions we have found that on the same substrate and under otherwise identical reaction conditions the required amount of the new catalyst can be lowered to a fragment of the amount of similar known catalysts (from 1-5 mole % related to the substrate to 0.1-0.3 mole % related to the substrate) without any remarkable decrease in yield and conversion attained under the same reaction time. Although the yield and conversion attained under the same reaction conditions under a given reaction time decreases when the amount of catalyst is further lowered below this level, this can be well counterbalanced by increasing the temperature and/or time of the reaction. As an example: in a Suzuki coupling of 2-bromo-pyridine with 2-(4-ethoxy-3-methyl-phenyl)-1,3,2-dioxaborolane performed in a 10:1 v/v mixture of methanol and water in the presence of $K_2CO_3$ at 110° C. under pressure 100% conversion was attained within 1 hour when using 0.25 mole % of the catalyst of formula (I). When lowering the amount of the catalyst to 0.05 mole % (which is 20% of the former value) the conversion attained within 1 hour still remained rather high (81%), and when using only 0.005 mole % of the catalyst (which is 2% of the former value and 1-5 thousandth of the usual industrial values) a conversion of 50% could even be attained within 1 hour.

In most instances it is not required to remove palladium from the product, because, owing to the low amount and high stability of the new catalyst, no palladium remains in the product, or the amount of residual palladium is below the acceptable level. Should residual palladium still be removed, the expensive scavenger methods [specific operations for binding Pd(0)] routinely used for this purpose can be fully omitted. The residual, still complexed palladium can be removed by simple operations (chromatography; filtration through an inexpensive carbon filter, etc.) routinely used in industry, and usually no more than one purification step is required.

The invention relates further to a method for preparing the compound of formula (I).

The catalyst of formula (I) can be readily prepared by reacting a palladium(II) salt with at least fourfold molar excess of tri-[3,5-bis(trifluoromethyl)-phenyl]-phosphine and reducing palladium(II) to palladium(0) in the resulting complex salt in a one-pot reaction. As palladium(II) salt preferably palladium dichloride can be used; a preferred reducing agent is hydrazine hydrate.

Tri-[3,5-bis(trifluoromethyl)-phenyl]-phosphine used as complexing agent is a known substance [see e.g. H. G. Alt, R. Baumgaertner, H. A. Brune: Chemische Berichte 119(5), 1694-1703 (1986)].

The invention also relates to the use of the compound of formula (I) as catalyst in C—C and C-heteroatom coupling reactions as well as for hydrogenation. We have found that the compound of formula (I) can be used in any type of these reactions. The conditions of such reactions may be the same as applied when using other Pd(0) complex catalysts, with the difference that when using the compound of formula (I) as catalyst usually lower, sometimes much lower amounts of catalyst are still sufficient to perform the reaction. Based on this general knowledge and on the information presented in this description, one skilled in the art can easily determine optimum parameters for reactions utilizing the catalyst of formula (I), by applying routine methods or sometimes simple tests and taking into account the dissolution characteristics of the catalyst. It should be noted here that the idea using the in situ prepared catalyst of formula (I) (for example $Pd_2(dba)_3$ with $PPh_3(CF_3)_6$) is not viable, because of the uncontrolled formation of the complex and of the almost immediate appearance of Pd-black results in poor yields.

The following Examples serve to illustrate further details of the invention.

EXAMPLE 1

Preparation of the Catalyst of Formula (I)

Argon was bubbled through 30 ml of dimethyl sulphoxide at room temperature, and then 6.7 g (0.01 mole) of tri-[3,5-bis(trifluoromethyl)-phenyl]-phosphine and 0.355 g (0.002 mole) of palladium(II) chloride were added. Thereafter the mixture was heated to 110-130° C. When a fully clear solution was obtained, indicating that a complex was formed, 0.5 g (0.01 mole) of hydrazine hydrate was added to the mixture. Thereafter the flask was immersed into ice water. The separated product was filtered through a sintered glass filter and washed three times with chloroform. A bright lemon yellow coloured crystalline solid was obtained with a yield of 90%.

Characteristic data of NMR spectra: $^1$H-NMR (300 MHz, THF-d$_8$, δ=3.58 ppm) 8.17 (s, 12 H), 7.84 (s, 24 H); $^{13}$C-

NMR (75 MHz, THF-d$_8$, δ=67.3 ppm) 138.1 (C), 133.7 (q, J=38.7 Hz, C), 133.4 (CH), 126.3 (CH), 123.4 (q, J=271.57 Hz, CF$_3$); $^{31}$P-NMR (300 MHz, THF-d$_8$) 28.77; $^{19}$F-NMR (300 MHz, THF-d$_8$)-62.94.

EXAMPLE 2

Preparation of
2-(4-ethoxy-3-methyl-phenyl)-pyridine by Suzuki Coupling Using a 10/1 v/v Mixture of Methanol and Water as Solvent and the Compound of Formula (I) as Catalyst General Prescription:

An amount of the catalyst of formula (I) to be given below, 618 mg (3 mmoles) of 2-(4-ethoxy-3-methyl-phenyl)-1,3,2-dioxaborolane and 553 mg (4 mmoles) of potassium carbonate were weighed into a flask. Thereafter the flask was placed under argon atmosphere, and 10 ml of methanol and 1 ml of water were added. Finally 316 mg (190 μl, 2 mmoles) of 2-bromo-pyridine (substrate) were introduced with an automatic pipette. The flask was closed, and the reaction mixture was stirred at a temperature and for a time to be given below, optionally under superatmospheric pressure.

For processing purposes, the cooled reaction mixture was extracted four times with 5 ml of chloroform, each; in this way almost the full amount of catalyst was removed from the product. As the chloroform extract still contained dioxoborolane impurity, the thus separated substance was further purified by silica gel column chromatography, utilizing a 3/1 v/v mixture of hexane and ethyl acetate as eluting agent.

Test Series (A):

In this test series the reactions were performed at 110° C. temperature and under superatmospheric pressure for 1 hour. The amount of the compound of formula (I) was varied, and it was examined how this variation influences the conversion attained.

In all of the cases presented in this description conversion values were determined on the basis of $^1$H NMR spectra or by gas chromatography. The results are summarized in Table 1. Although with these rather small scale test reactions the processing of the mixture influences the isolated yield, these data are also given for information purposes.

TABLE 1

| Amount of the catalyst | | Conversion attained | Isolated |
|---|---|---|---|
| mg | mole % related to the substrate | within 1 hour | yield, % |
| 56 | 1 | 100 | 89 |
| 28 | 0.5 | 100 | 87 |
| 14 | 0.25 | 100 | 88 |
| 2.8* | 0.05 | 81 | 69 |
| 0.28* | 0.005 | 50 | 39 |

*The catalyst was added to the mixture as a stock solution formed with tetrahydrofuran.

No separation of palladium black was observed in any of the cases; the colour of the reaction mixture remained lemon yellow in all of the reactions. It is particularly remarkable that a 50% conversion could still be attained within 1 hour when the amount of the catalyst of formula (I) was as low as 0.005 mole %. According to our experiences gathered in other tests this decrease in conversion can be counterbalanced by increasing the time and/or the temperature of the reaction.

In tests performed for checking purposes the above reaction was repeated so that no catalyst was added to the reaction mixture. In this way we intended to ascertain that the formation of the product can indeed be attributed to the catalyst administered in a very low amount, and not to the effect of any metal impurities which might be present in the solvents or in the flasks. Under these conditions the conversion was zero, thus it can be stated with full certainty that the catalyst of formula (I) is active even in an amount of 0.005 mole %.

Test Series (B):

In this test series 0.25 mole % of the catalyst of formula (I) was used for 1 mole of 2-bromo-pyridine substrate, and the reactions were performed for 1 hour at temperatures listed in Table 2, under superatmospheric pressure if required. It was examined how the changes in temperature influence the conversion attained. The results are listed in Table 2; the isolated yields are also given for information purposes.

TABLE 2

| Temperature, ° C. | Conversion attained within 1 hour, % | Isolated yield, % |
|---|---|---|
| 25 | 0 | 0 |
| 50 | 5 | not measured |
| 70 | 25 | 16 |
| 90 | 60 | 47 |
| 110 | 100 | 88 |

The observed results show that when using a 10/1 v/v mixture of methanol and water as reaction medium, it is advisable to perform the coupling reaction at temperatures above 90° C. and under superatmospheric pressures which enable the reaction mixture to remain liquid. This can be explained by the fact that a remarkable dissolution of the catalyst occurs at such temperatures. Formation of palladium black or any other sign of catalyst decomposition could not be observed in any of the reactions. As a comparison: when in the reaction performed at 110° C. the catalyst of formula (I) was replaced by the same amount of the catalyst of formula (II), the reaction mixture got black within some minutes. After terminating the reaction it is very difficult to remove metal impurities. The product obtained in this latter reaction remained orange yellow/dark orange yellow even after full removal of palladium black, whereas when using the catalyst according to the invention snow white product was obtained.

The physical constants of all of the product samples obtained in Example 2 were, within the limits of measurement accuracy, in good agreement with one another and with the respective parameters of the authentic product sample. For information purposes we present below the physical constants measured by us on a 2-(4-ethoxy-3-methoxy-phenyl)-pyridine sample prepared in a 10/1 v/v mixture of methanol and water at 110° C. for 1 hour utilizing 0.25 mole % of the catalyst of formula (I):

$^1$H NMR (300 MHz, CDCl$_3$, δ$_{TMS}$=0 ppm): 8.65 (d, J=4.8 Hz, 1H), 7.75 (m, 4H), 7.16 (m, 1H), 6.90 (d, J=8.4 Hz, 1H), 4.10 (q, J=6.9 Hz, 2H), 2.31 (s, 3H), 1.45 (t, J=7.2 Hz).

$^{13}$C-NMR (75 MHz, CDCl$_3$, δ$_{CDCl3}$=77.00 ppm): 158.2 (C), 157.3 (C), 149.3 (CH), 136.7 (CH), 131.1 (C), 129 (CH), 127.1 (C), 125.5 (CH), 121.2 (CH), 119.9 (CH), 111.0 (CH), 63.6 (CH$_2$), 16.4 (CH$_3$), 14.9 (CH$_3$).

IR (KBr, ν cm$^{-1}$): 1604, 1587, 1561, 1467, 1433, 1394, 1309, 1281, 1247, 1181, 1151, 1131, 1109, 1042, 926, 884, 777, 742, 618.

EXAMPLE 3

Preparation of 2-(4-ethoxy-3-methyl-phenyl)-pyridine by Suzuki Coupling in Reaction Media Other than a 10/1 v/v Mixture of Methanol and Water and Using the Compound of Formula (I) as Catalyst The Suzuki coupling described in Example 2 was repeated using 316 mg (190 µl, 2 mmoles) of 2-bromo-pyridine as substrate and a total amount of 11 ml of reaction medium, however, the reaction conditions (composition of the reaction mixture; amount of the catalyst; amount of the dioxoborolane reagent; reaction time; temperature) were varied as indicated in Table 3. The conversion was measured as described in Example 2. The results are listed in Table 3.

TABLE 3

| Solvent 10 ml/1 ml | Catalyst mg/mole % | Time hour | Dioxo boro- lane, equiv. | Temperature °C. | Conversion % |
|---|---|---|---|---|---|
| EtOH/H₂O | 14/0.25 | 1 | 1.5 | 110 | 100 |
| iPrOH/H₂O | 14/0.25 | 1 | 1.5 | 110 | 100 |
| tBuOH/H₂O | 14/0.25 | 1 | 1.5 | 110 | 100 |
| Hexan/H₂O | 14/0.25 | 1 | 1.5 | 110 | 27 |
| DME/H₂O | 14/0.25 | 1 | 1.5 | 110 | 48 |
| THF/H₂O | 14/0.25 | 1 | 1.5 | 110 | 85 |
| THF/H₂O | 0.112/0.002 | 19 | 1.5 | 110 | 26 |
| THF/H₂O | 0.112/0.002 | 72 | 1.5 | 110 | 78 |
| THF/H₂O | 0.112/0.002 | 1 | 1.5 | 130 | 39 |
| THF/H₂O | 0.112/0.002 | 3 | 1.5 | 130 | 74 |
| THF/H₂O | 0.112/0.002 | 19 | 1.5 | 130 | 100 |
| THF/H₂O | 0.112/0.002 | 3 | 1.1 | 130 | 33 |

When aqueous ethanol, aqueous isopropanol and aqueous tert.butanol were used, during the reaction time of 1 hour the colour of the reaction mixture gradually deepened and got brown; the order of deepening order was ethanol-isopropanol-tert.butanol. However, no palladium black separated in any of the instances, and the conversion remained 100%, reflecting that the catalyst retained its activity. When conducting the reaction in hexane/water, dimethoxyethane/water and tetrahydro-furan/water mixtures we have found that the quality of the organic solvent component of the reaction mixture highly influences the conversion attainable within a given period of time. This is a usual phenomenon with cross coupling reactions. Again, no formation of palladium black could be observed with these solvents, although sometimes the colour of the reaction mixture deepened during the reaction. The results of the tests performed in tetrahydrofuran/water mixture are particularly remarkable. The test was also done with an extremely low amount of catalyst (0.002 mole %; about one thousandth of the amount required from known catalysts). Like in Example 2, this extremely low amount of catalyst was introduced into the mixture as a stock solution in tetrahydrofuran. The data clearly indicate that the decrease in conversion can be well counterbalanced by increasing the reaction time and/or the reaction temperature: upon raising the temperature to 130° C. and the reaction time to 19 hours 100% conversion could be attained even with this extremely low amount of catalyst. Upon performing the checking test described in Example 2 (reaction without catalyst) we have ascertained again that product formation can be attributed solely to the presence of the catalyst, and not to the effect of any possible metal impurities which might be present in the solvents or in the flasks. The outstanding stability of the catalyst of formula (I) is well illustrated by the fact that no sign of catalyst decomposition could be observed even after a reaction performed at 130° C. for 19 hours, which is a very drastic condition.

EXAMPLE 4

Preparation of Pyridine Derivatives by Suzuki Coupling, Using the Catalyst of Formula (I)

General Prescription:

14 mg (0.25 mole % related to the 2-bromo-pyridine substrate) of the catalyst of formula (I), 3 mmoles of the dioxaborolane reagent and 553 mg (4 mmoles) of potassium carbonate were weighed into a flask. Thereafter the flask was placed under argon atmosphere, and 10 ml of methanol and 1 ml of water were added. Finally 316 mg (190 µl, 2 mmoles) of 2-bromo-pyridine (substrate) were introduced with an automatic pipette. The flask was then closed, and the reaction mixture was stirred for 1 hour at 110° C. under a pressure required to maintain a liquid reaction mixture. Thereafter the reaction mixture was processed as described in Example 2.

The reactants used, the products obtained and their physical constants, as well as the isolated yields (%) are listed in Table 4.

TABLE 4

| Product | Reactant | ¹H-NMR (300 MHz, CDCl₃) | Yield, % |
|---|---|---|---|
| 2-(4-Methoxy-3-methyl-phenyl)-pyridine | 2-(4-Methoxy-3-methyl-pheny)-1,2,3-dioxaborolane | 8.65 (d, J = 4.5 Hz, 1H), 7.80 (m, 7.70 (m, 2H), 7.14 (m, 1H), 6.91 (d, J = 8.1 Hz, 1H), 3.88 (s, 3H). 2.30 (s, 3H) | 73 |
| 2-(3,4-Dimethoxy-phenyl)-pyridine | 2-(3,4-Dimethoxy-phenyl)-boronic acid | 8.65 (d, J = 4.5 Hz, 1H), 7.69 (m, 3H), 7.5 (d, J = 8.1 Hz, 1H), 7.18 (m, 1H), 6.59 (d, J = 8.1 Hz, 1H), 3.99 (s, 3H) | 75 |
| 2-(4-Methoxy-phenyl)-pyridine | 2-(4-Methoxy-phenyl)-1,3,2-dioxaborolane | 8.65 (d, J = 4.8 Hz, 1H), 7.94 (d, J = 9 Hz, 2H), 7.69 (m, 2H), 7.16 (m, 1H), 6.99 (d, J = 8.7 Hz, 2H), 3.85 (s, 3H) | 58 |

TABLE 4-continued

| Product | Reactant | $^1$H-NMR (300 MHz, CDCl$_3$) | Yield, % |
|---|---|---|---|
| 2-(p-Tolyl)-pyridine | 2-(p-Tolyl)-1,3,2-dioxaborolane | 8.68 (d, J = 4.5 Hz, 1H), 7.90 (d, J = 8.4 Hz, 2H), 7.73 (m, 2H), 7.26 (m, 2H), 7.21 (m, 1H), 2.41 (s, 3H) | 62 |
| 2-(4-Fluoro-phenyl)-pyridine | 2-(4-Fluoro-phenyl)-1,3,2-dioxaborolane | 8.67 (d, J = 4.8 Hz, 1H), 7.98 (m, 3H) | 26 90* |

*Yield attained after 16 hours of reaction

The physical constants of all of the obtained products were, within the limits of measurement accuracy, in good agreement with the respective parameters of the authentic product samples. The reaction mixtures always remained lemon yellow, even after a reaction time of 16 hours. No sign referring to an optional decomposition of the catalyst could be detected.

EXAMPLE 5

Preparation of Indole Derivatives by Suzuki Coupling, Using the Catalyst of Formula (I)

General Prescription:

14 mg (0.25 mole % related to the 5-bromo-indole substrate) of the catalyst of formula (I), 3 mmoles of the dioxaborolane reagent, 553 mg (4 mmoles) of potassium carbonate and 390 mg (2 mmoles) of 5-bromo-indole were weighed into a flask. Thereafter the flask was placed under argon atmosphere, and 10 ml of methanol and 1 ml of water were added. The flask was then closed, and the reaction mixture was stirred for 1 hour at 110° C. under a pressure required to maintain a liquid reaction mixture.

Of the end-products obtained only 5-(p-tolyl)-1H-indole is soluble in water. When preparing this compound, the reaction mixture was processed as described in Example 2.

The reaction mixtures comprising other (water insoluble) indole compounds were processed as follows:

9 ml of water were added to the reaction mixture, and the separated solid, which comprises the catalyst and the product, was filtered off through a sintered glass filter. In order to remove the catalyst, the resulting solid was dissolved in chloroform, the chloroform-insoluble catalyst was filtered off, the filtrate was dried over sodium sulphate and evaporated then in vacuo.

The reactants used, the products obtained and their physical constants, as well as the isolated yields (%) are listed in Table 5.

TABLE 5

| Product | Reactant | $^1$H-NMR (300 MHz, CDCl$_3$) | Yield, % |
|---|---|---|---|
| 5-(4-Ethoxy-3-methyl-phenyl)-1H-indole | 2-(4-Ethoxy-3-methyl-phenyl)-1,3,2-dioxaborolane | 8.10 (bs, 1H), 7.83 (s, 1H), 7.43 (m, 4H), 7.22 (m, 1H), 6.91 (d, J = 8.4 Hz, 1H), 6.61 (s, 1H), 4.11 (q, J = 6.9 Hz, 2H), 2.34 (s, 3H), 1.48 (t, J = 6.9 Hz, 3H) | 93 |
| 5-(4-Methoxy-3-methyl-phenyl)-1H-indole | 2-(4-Methoxy-3-methyl-phenyl)-1,3,2-dioxaborolane | 8.13 (bs, 1H), 7.82 (s, 1H), 7.44 (m, 4H), 7.22 (m, 1H), 6.92 (d, J = 9 Hz, 1H), 6.60 (s, 1H), 3.89 (s, 1H), 2.32 (s, 3H) | 90 |
| 5-(4-Methoxy-phenyl)-1H-indole | 2-(4-Methoxy-phenyl)-1,3,2-dioxaborolane | 8.12 (bs, 1H), 7.84 (s, 1H), 7.60 (m, 2H), 7.44 (s, 2H), 7.22 (t, J = 3 Hz, 1H), 7.02 (m, 2H), 6.62 (t, J = 2.4 Hz, 1H), 3.83 (s, 3H) | 87 |
| 5-(3,4-Dimethoxy-phenyl)-1H-indole | 2-(3,4-Dimethoxy-phenyl)-boronic acid | 82 (bs, 1H), 7.81 (s, 1H), 7.42 (s, 2H), 7.21 (m, 3H), 6.95 (d, J = 8.7 Hz, 1H), 6.59 (m, 1H), 3.96 (s, 3H), 3.92 (s, 3H) | 94 |
| 5-(p-Tolyl)-1H-indole | 2-(p-Tolyl)-1,3,2-dioxaborolane | 8.13 (bs, 1H), 7.87 (s, 1H), 7.58 (d, J = 8.1 Hz, 2H), 7.45 (m, 2H), 7.28 (d, J = 8.4 Hz, 2H), 7.24 (m, 1H), 6.6 (m, 1H), 2.43 (s, 3H) | 92 |
| 5-Phenyl-1H-indole | Phenylboronic acid | 8.12 (bs, 1H), 7.90 (s, 1H), 7.70 (d, J = 7.2 Hz, 2H), 7.47 (m, 4H), 7.35 (m, 1H), 7.24 (m, 1H), 6.64 (m, 1H) | 84 |
| 5-(4-Fluoro-phenyl)-1H-indole | 2-(4-Fluoro-phenyl)-1,3,2-dioxaborolane | 8.13 (bs, 1H), 7.84 (s, 1H), 7.62 (m, 2H), 7.43 (m, 2H), 7.24 (m, 1H), 7.16 (m, 2H), 6.64 (m, 1H) | 77 |

The physical constants of all of the obtained products were, within the limits of measurement accuracy, in good agreement with the respective parameters of the authentic product samples. No appearance of palladium black was observed in the reaction mixtures; the separated catalyst always remained lemon yellow.

EXAMPLE 6

Preparation of Isoquinoline Derivatives by Suzuki Coupling, Using the Catalyst of Formula (I)

General Prescription:
14 mg (0.25 mole % related to the 5-bromo-isoquinoline substrate) of the catalyst of formula (I), 3 mmoles of the dioxaborolane reagent, 553 mg (4 mmoles) of potassium carbonate and 416 mg (2 mmoles) of 5-bromo-isoquinoline were weighed into a flask. Thereafter the flask was placed under argon atmosphere, and 10 ml of methanol and 1 ml of water were added. The flask was then closed, and the reaction mixture was stirred for 1 hour at 110° C. under a pressure required to maintain a liquid reaction mixture. The resulting reaction mixtures were processed as described in Example 2.

The reactants used, the products obtained and their physical constants, as well as the isolated yields (%) are listed in Table 6.

The physical constants of all of the obtained products were, within the limits of measurement accuracy, in good agreement with the respective parameters of the authentic product samples. The reaction mixtures always remained lemon yellow, and no sign referring to an optional decomposition of the catalyst could be detected.

EXAMPLE 7

Preparation of Biphenyl Derivatives by Suzuki Coupling, Using the Catalyst of Formula (I)

General Prescription:
14 mg (0.25 mole % related to the p-bromo-toluene substrate) of the catalyst of formula (I), 3 mmoles of the dioxaborolane reagent, 553 mg (4 mmoles) of potassium carbonate and 342 mg (2 mmoles) of p-bromo-toluene were weighed into a flask. Thereafter the flask was placed under argon atmosphere, and 10 ml of methanol and 1 ml of water were added. The flask was then closed, and the reaction mixture was stirred for 1 hour at 110° C. under a pressure required to maintain a liquid reaction mixture. The resulting reaction mixtures were processed as described in Example 5.

The reactants used, the products obtained and their physical constants, as well as the isolated yields (%) are listed in Table 7.

TABLE 6

| Product | Reactant | $^1$H-NMR (300 MHz, CDCl$_3$) | Yield, % |
|---|---|---|---|
| 5-(4-Ethoxy-3-methyl-phenyl)-isoquinoline | 2-(4-Ethoxy-3-methyl-phenyl)-1,3,2-dioxaborolane | 9.22 (s, 1H), 8.40 (d, J = 6 Hz, 1H) 7.87 (m, 1H), 7.70 (d, J = 6 Hz, 1H) 7.50 (d, J = 6 Hz, 1H), 7.10 (d, J = 6 Hz, 1H), 6.87 (d, J = 9 Hz, 1H), 4.05 (q, J = 6.9 Hz, 2H), 2.24 (s, 3H), 1.41 (t, J = 6.9 Hz, 3H) | 89 |
| 5-(4-Methoxy-3 methyl-phenyl)-isoquinoline | 2-(4-Methoxy-3-methyl-phenyl)-1,3,2-dioxaborolane | 9.29 (s, 1H), 8.48 (d, J = 6 Hz, 1H) 7.95 (m 1H), 7.77 (d, J = 6 Hz, 1H), 7.60 (m, 2H), 7.28 (m, 2H), 6.96 (d, J = 8.7 Hz, 1H), 3.92 (s, 3H), 2.32 (s, 3H) | 85 |
| 5-(3,4-Dimethoxy-phenyl)-isoquinoline | 3,4-Dimethoxy-phenyl-boronic acid | 9.31 (bs, 1H), 8.47 (m, 1H), 7.95 (m, 1H), 7.78 (d, J = 6 Hz, 1H), 7.65 (m, 2H), 7.00 (m, 3H), 3.97 (s, 3H), 3.91 (s, 3H) | 89 |
| 5-(4-Methoxy-phenyl)-isoquinoline | 2-(4-Methoxy-phenyl)-1,3,2-dioxaborolane | 9.30 (s, 1H), 8.48 (d, J = 6 Hz, 1H) 7.97 (m, 1H), 7.75 (d, J = 6 Hz, 1H), 7.41 (s, 2H), 7.05 (m, 2H), 3.90 (s, 3H) | 57 90* |
| 5-(p-Tolyl)-isoquinoline | 2-(p-Tolyl)-1,3,2-dioxaborolane | 9.31 (s, 1H), 8.48 (d, J = 6.3 Hz, 1H), 7.98 (m, 1H), 7.75 (d, J = 6 Hz, 1H), 7.66 (m, 2H), 7.35 (m, 4H), 2.43 (s, 3H) | 59 91* |
| 5-(4-Fluoro-phenyl)-isoquinoline | 2-(4-Fluoro-phenyl-1,3,2-dioxaborolane | 9.3 (s, 1H), 8.49 (d, J = 6.3 Hz, 1H), 7.97 (m, 1H), 7.62 (m, 3H), 7.42 (m, 2H), 7.22 (m, 2H) | 56 |

*Yield attained after 3 hours of reaction.

TABLE 7

| Product | Reactant | $^1$H-NMR (300 MHz, CDCl$_3$) | Yield, % |
|---|---|---|---|
| 4-Ethoxy-3,4'-di-methyl-biphenyl | 2-(4-Ethoxy-3-methyl-phenyl)-1,3,2-dioxaborolane | 7.48 (m, 2H), 7.37 (m, 2H), 7.24 (m, 2H), 6.88 (m, 1H), 4.09 (q, J = 6.9 Hz, 2H), 2.41 (s, 3H), 2.32 (s, 3H), 1.47 (t, J = 6.9 Hz) | 95.5 |
| 4-Methoxy-3,4'-di-methyl-biphenyl | 2-(4-Methoxy-3-methyl-phenyl)-1,3,2-dioxaborolane | 7.48 (m, 2H), 7.42 (m, 2H), 7.25 (m, 2H), 3.89 (s, 3H), 2.42 (s, 3H), 2.33 (s, 3H) | 97 |

The physical constants of all of the obtained products were, within the limits of measurement accuracy, in good agreement with the respective parameters of the authentic product samples. The reaction mixtures always remained lemon yellow, and no sign referring to an optional decomposition of the catalyst could be detected.

EXAMPLE 8

Preparation of Stilbene Derivatives by Heck Coupling, Using the Catalyst of Formula (I)

Stilbene derivatives were prepared by reacting styrene with various aryl bromides as shown in the following reaction scheme:

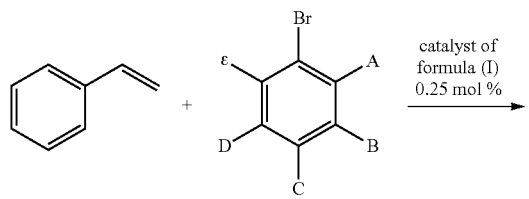

-continued

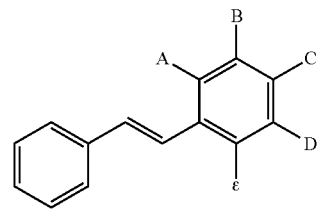

General Prescription:

552 mg (4 mmoles, 2 eq.) of K$_2$CO$_3$, 14 mg (0.25 mole % calculated for the aryl bromide substrate) of the catalyst of formula (I), 312 mg (0.343 ml, 3 mmoles, 1.5 eq) of styrene, 2 mmoles (1 eq.) of the aryl bromide substrate and 10 ml of a 10:1 mixture of methanol and water were charged into an oven-dried Schlenk tube. The reaction was performed at 110° C. for 3 hours or 20 hours, as shown in Table 8. The conversions were determined by subjecting the reaction mixtures to GC, and the product was then isolated. For tests Nos. 1, 2, 3 and 5 the products precipitated from the mixture upon cooling, thus they could be isolated by a simple filtration; whereas for tests Nos. 4, 6 and 7 the products were isolated by flash chromatography.

The results are summarized in Table 8.

TABLE 8

| Test No. | Aryl bromide | | | | | Conversion, % | | Isolated yield, % |
|---|---|---|---|---|---|---|---|---|
| | A | B | C | D | E | 3 hours | 20 hours | |
| 1 | H | F | H | H | H | 95 | — | 73 |
| 2 | H | H | NO$_2$ | H | H | 100 | — | 67 |
| 3 | H | H | Me | H | H | 100 | — | 93 |
| 4 | OMe | H | OMe | H | H | 57 | 78 | 60 |
| 5 | H | Me | H | Me | H | 98 | — | 96 |
| 6 | Me | H | H | H | Me | 53 | 64 | 38 |
| 7 | iPr | H | iPr | H | iPr | 90 | — | 33 |

The NMR data of the resulting stilbene derivatives are as follows:

(E)-3-Fluorostilbene: $^1$H NMR (300 MHz, CDCl$_3$) δ 7.53 (d, J=7.5 Hz, 2H), 7.39 (t, J=7.5 Hz, 2H), 7.41-7.22 (m, 4H), 7.11 (s, 1H), 7.10 (s, 1H), 6.99-6.94 (m, 1H); $^{13}$C NMR (ATP) (75 MHz, CDCl$_3$) δ 163.5 (C, d, J=244 Hz), 139.9 (C, d, J=7.65 Hz), 137.1 (C), 130.3 (CH, d, J=8.18 Hz), 129.0 (CH), 128.2 (CH), 127.7 (CH, d, J=2.70 Hz), 126.9 (CH), 122.7 (CH, d, J=2.78 Hz), 114.62 (CH, d, J=21.5 Hz), 113.0 (CH, d, J=21.5 Hz).

(E)-4-Nitrostilbene: $^1$H NMR (300 MHz, CDCl$_3$) δ 8.23-8.21 (m, 2H), 7.63 (d, J=8.7 Hz, 2H), 7.55 (d, J=7.5 Hz, 2H), 7.43-7.25 (m, 4H), 7.14 (d, J=16.5 Hz, 1H); $^{13}$C NMR (ATP) (75 MHz, CDCl$_3$) δ 147.0 (C), 136.4 (C), 133.6 (CH), 129.1 (CH), 127.3 (CH), 127.1 (CH), 126.5 (CH), 124.4 (CH).

(E)-4-Methylstilbene: $^1$H NMR (300 MHz, CDCl$_3$) δ 7.54 (d, J=7.8 Hz, 2H), 7.46 (d, J=7.8 Hz, 2H), 7.41-7.36 (m, 2H), 7.31-7.26 (m, 1H), 7.21 (d, J=7.8 Hz, 2H), 7.12) s, 2H), 2.40 (s, 3H); $^{13}$C NMR (ATP) (75 MHz, CDCl$_3$) δ 137.8 (C), 137.8 (C), 134.8 (C), 129.7 ((CH), 128.9 (CH), 128.0 (CH), 127.7 (CH), 126.7 (CH), 21.5 (CH$_3$).

(E)-2,4-Dimethoxystilbene: $^1$H NMR (300 MHz, CDCl$_3$) δ 7.53 (d, J=8.4 Hz, 3H), 7.42 (d, J=16.5 Hz, 1H), 7.35 (t, J=7.5 Hz, 2H), 7.24 (dd, J=4.9 Hz, 12.1 Hz, 1H), 7.02 (d, J=16.5 Hz, 1H), 6.53 (dd, J=2.2 Hz, 9.9 Hz, 1H), 6.49 (d, J=2.4 Hz, 1H), 3.88 (s, 1H), 3.84 (s, 1H); $^{13}$C NMR (ATP) (75 MHz, CDCl$_3$) δ 160.5 (C), 138.3 (C), 128.5 (CH), 127.2 (CH), 127.0 (CH), 126.9 (CH), 126.3 (CH), 123.3 (CH), 119.5 (C), 105.0 (CH), 98.5 (CH), 55.5 (CH$_3$), 55.4 (CH$_3$).

(E)-3,5-Dimethylstilbene: $^1$H NMR (300 MHz, CDCl$_3$) δ 7.55-7.53 (m, 2H), 7.41-7.36 (m, 2H), 7.31-7.26 (m, 1H), 7.18 (s, 2H), 7.11 (d, J=2.4 Hz, 2H), 6.95 (s, 1H), 2.38 (s, 6H); $^{13}$C NMR (ATP) (75 MHz, CDCl$_3$) δ 138.3 (C), 137.5 (C), 129.7 (CH), 129.1 (CH), 128.9 (CH), 128.5 (CH), 127.7 (CH), 126.7 (CH), 124.7 (CH), 21.5 (CH$_3$).

(E)-2,6-Dimethylstilbene: $^1$H NMR (300 MHz, CDCl$_3$) δ 7.54-7.52 (m, 2H), 7.42-7.37 (m, 2H), 7.32-7.26 (m, 1H), 7.13 (d, J=16.8 Hz, 1H), 7.1 (m, 3H), (m, 3H), 6.63 (d, J=16.8 Hz, 1H), 2.39 (s, 6H); $^{13}$C NMR (ATP) (75 MHz, CDCl$_3$) δ 137.6 (C), 137.0 (C), 136.2 (C), 134.0 (CH), 128.7 (CH), 127.9 (CH), 127.6 (CH), 126.9 (CH), 126.7 (CH), 126.3 (CH), 21.0 (CH$_3$).

(E)-2,4,6-Triisopropylstilbene: $^1$H NMR (300 MHz, CDCl$_3$) δ 7.54-7.52 (m, 2H), 7.43-7.38 (m, 2H), 7.33-7.26 (m, 1H), 7.22 (d, J=16.5 Hz, 1H), 7.07 (s, 2H), 6.52 (d, J=16.8 Hz, 1H), 3.31 (h, J=6.9 Hz, 2H), 2.94 (h, J=6.9 Hz, 1H), 1.33-1.23 (m, 18H); $^{13}$C NMR (ATP) (75 MHz, CDCl$_3$) δ 142.4 (C), 141.4 (C), 132.3 (C), 128.6 (CH), 127.7 (C), 123.4 (CH), 122.1 (CH), 121.7 (CH), 121.0 (CH), 115.3 (CH), 29.0 (CH), 24.9 (CH), 18.7 (CH$_3$), 18.5 (CH$_3$).

EXAMPLE 9

Preparation of Phenylacetylene Derivatives by Sonogishara Coupling, Using the Catalyst of Formula (I)

Phenylacetylene derivatives were prepared by reacting phenylacetylene with various aryl bromides as shown in the following reaction scheme:

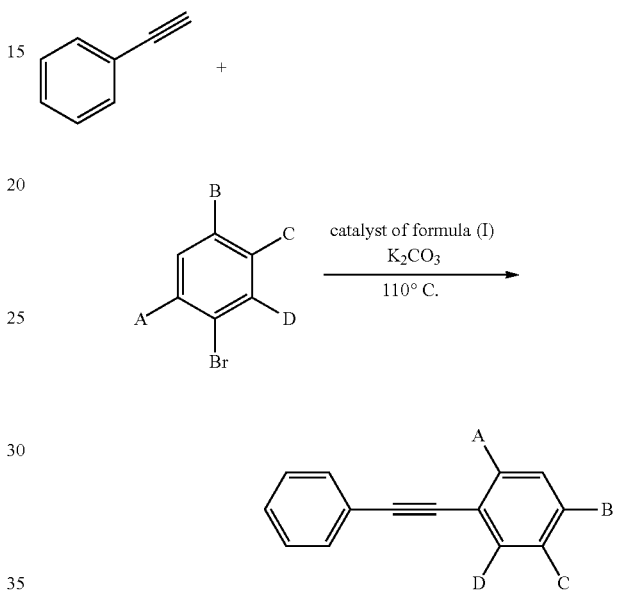

General Prescription:

276 mg (2 mmoles, 1 eq.) of K$_2$CO$_3$, 7 mg (0.25 mole % calculated for the aryl bromide substrate) of the catalyst of formula (I), 0.165 ml (1.5 mmoles, 1.5 eq) of phenylacetylene, 1 mmoles (1 eq.) of the aryl bromide substrate and 5 ml of the solvent [solvent (a): a 5:1 mixture of methanol and water; solvent (b): n-butanol; solvent (c): glycerol-formal] were charged into an oven-dried Schlenk tube. The reaction was performed at 110° C. for 3 hours or 24 hours, as shown in Table 9. The amounts of the products were determined by subjecting the reaction mixture to GC.

The results are summarized in Table 9.

TABLE 9

| Test No. | Aryl bromide | | | | Solvent | After 3 hours | | After 24 hours | |
|---|---|---|---|---|---|---|---|---|---|
| | A | B | C | D | | Conv. % | Product % | Conv. % | Product % |
| 1 | H | OMe | Me | H | (a) | 47 | 43 | 71 | 57 |
| 2 | H | NO$_2$ | H | H | (a) | 88 | 43 | 100 | 56 |
| 3 | H | CH$_3$ | H | H | (a) | 51 | 48 | 81 | 78 |
| 4 | iPr | iPr | H | iPr | (a) | 10 | 8 | 97 | 46 |
| 5 | H | OMe | Me | H | (b) | 91 | 65 | 100 | 66 |
| 6 | H | NO$_2$ | H | H | (b) | 100 | 78 | — | — |
| 7 | H | Me | H | H | (b) | 100 | 84 | — | — |
| 8 | iPr | iPr | H | iPr | (c) | 36 | 31 | 100 | 87 |

The NMR data of the resulting phenylacetylene derivatives are as follows:

1-Methyl-4-(phenylethynyl)-benzene: $^1$H NMR (300 MHz, CDCl$_3$) δ 7.43 (d, J=8.0 Hz, 2H), 7.26-7.22 (m, 5H), 6.70 (d, J=8.3 Hz, 1H), 3.75 (s, 3H), 2.13 (s, 3H); $^{13}$C NMR (ATP) (75 MHz, CDCl$_3$) δ 158.2 (C), 133.9 (CH), 131.5 (CH), 130.6 (CH), 128.5 (CH), 128.3 (CH), 127.9 (CH), 123.8 (C), 109.9 (CH), 89.9 (C), 55.4 (CH), 16.1 (CH).

1-Nitro-4-(phenylethynyl)-benzene: $^1$H NMR (300 MHz, CDCl$_3$) δ 8.17 (d, J=9.0 Hz, 2H), 7.62 (d, J=9.0 Hz, 2H), 7.58-7.55 (m, 2H), 7.41-7.38 (m, 3H); $^{13}$C NMR (ATP) (75 MHz, CDCl$_3$) δ 147.0 (C), 132.3 (CH), 131.9 (CH), 130.3 (C), 129.4 (CH), 129.0 (CH), 123.7 (CH), 122.2 (C), 94.8 (C), 87.7 (C).

1-Methyl-4-(phenylethynyl)-benzene: $^1$H NMR (300 MHz, CDCl$_3$) δ 7.60-7.57 (m, 2H), 7.49 (d, J=8.1 Hz, 2H), 7.40-7.35 (m, 3H), 7.20 (d, J=7.9 Hz, 2H), 2.41 (s, 3H); $^{13}$C NMR (ATP) (75 MHz, CDCl$_3$) δ 138.6 (C), 131.8 (CH), 131.7 (CH), 129.3 (CH), 128.5 (CH), 128.3 (CH), 123.7 (C), 120.4 (C), 89.8 (C), 89.0 (CH), 21.7 (CH$_3$).

Phenyl-(2,4,6-triisopropyl-phenyl)-acetylene: $^1$H NMR (300 MHz, CDCl$_3$) δ 7.58 (dd, J=8.0 Hz, 1.4 Hz, 2H), 7.43-7.35 (m, 3H), 7.07 (s, 2H), 3.65 (sept, J=6.9 Hz, 2H), 2.96 (sept, J=6.9 Hz, 1H), 1.36 (d, J=6.9 Hz, 12H), 1.32 (d, J=6.9 Hz, 6H);
$^{13}$C NMR (ATP) (75 MHz, CDCl$_3$) δ 150.9 (C), 149.5 (C), 131.5 (CH), 128.6 (CH), 128.1 (CH), 124.6 (CH), 120.7 (CH), 118.7 (C), 97.0 (C), 87.3 (C), 4.9 (CH$_3$), 32.2 (CH$_3$), 24.2 (CH$_3$), 23.6 (CH$_3$).

The above reaction was repeated by using 2-bromo-3-methyl-but-2-ene as substrate. The obtained results are listed in Table 10.

TABLE 10

| Test No. | Solvent | After 3 hours Conversion, % | Product, % | After 24 hours Conversion, % | Product, % |
|---|---|---|---|---|---|
| 1 | (a) | 22 | 10 | 64 | 40 |
| 2 | (b) | 24 | 15 | 84 | 28 |
| 3 | (c) | 93 | 87 | 100 | 94 |

The NMR data of the resulting product are as follows: $^1$H NMR (300 MHz, CDCl$_3$) δ 7.45-7.39 (m, 2H), 7.34-7.22 (m, 3H), 2.02 (s, 3H), 1.89 (s, 3H), 1.79 (s, 3H).

EXAMPLE 10

Preparation of N-Phenyl-Piperidine by Buchwald Reaction, Using the Compound of Formula (I) as Catalyst 224 mg (2 mmoles) of potassium tert.-butoxide, 70 mg (2.5 mole % calculated for the bromobenzene substrate) of the catalyst of formula (I), 105 μl (1 mmole) of bromobenzene, 198 μl (2 mmoles) of piperidine and 5 ml of solvent were charged into an oven-dried Schlenk tube. The reaction mixture was heated on an oil bath at 110° C. for 24 hours, allowed then to cool to room temperature, and evaporated under reduced pressure. The residue was purified by column chromatography on silica gel (eluant: hexane/ethyl acetate) to give the desired product; $^1$H NMR (300 MHz, CDCl$_3$) δ 7.31-7.26 (m, 2H), 7.00-6.97 (m, 2H), 6.89-6.84 (m, 1H), 3.19 (t, J=5.6 Hz, 4H), 1.79-1.72 (m, 4H), 1.64-1.59 (m, 2H).

The results of the tests performed in different solvents are summarized in Table 11.

TABLE 11

| Test No. | Solvent | Conversion, % after 3 hours | after 24 hours |
|---|---|---|---|
| 1 | toluene | 40 | 47 |
| 2 | DMSO | 35 | 37 |

What we claim is:

1. A composition comprising a palladium(0)-tris{tri-[3,5-bis(trifluoromethyl)-phenyl]-phosphine} complex of formula (I)

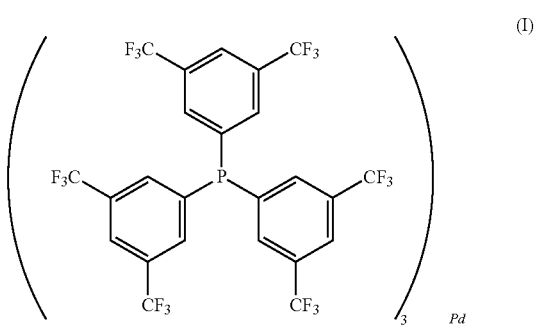

exhibiting a stability characterized by no measurable decomposition on the basis of $^{31}$P, $^{19}$F, $^{13}$C and $^1$H NMR spectra following at least 4 months of storage in air at a temperature of at least 25° C.

2. The composition of claim 1 in a solid form.

3. The composition of claim 1 having a melting point of 220° C. as determined by DSC in inert atmosphere.

4. The composition of claim 1, having a decomposition point of 169.5° C. as determined by DSC in air under atmospheric pressure.

5. The palladium(0) complex of claim 1 exhibiting a stability characterized by no measurable decomposition on the basis of $^{31}$P, $^{19}$F, $^{13}$C and $^1$H NMR spectra following 20 months of storage in air at room temperature.

6. The palladium(0) complex of claim 1 having a melting point in inert atmosphere of 220° C.

7. The palladium(0) complex of claim 1 exhibiting stability at any temperature below its melting point.

8. The palladium(0) complex of claim 1 exhibiting insolubility in water at industrially relevant temperatures and stability when stored in water.

9. The palladium(0) complex of claim 1 comprising a yellow solid.

10. The palladium(0) complex of claim 1 that dissolves at around 90° C. in aqueous alcohols.

11. The palladium(0) complex of claim 1 having catalytic activity in cross coupling reactions at a concentration of from 0.1 to 0.3 mole % of the substrate.

12. A method for catalysing a C—C, C-heteroatom, or hydrogenation reaction comprising carrying out the C—C, C-heteroatom or hydrogenation reaction in the presence of the palladium(0) complex of claim 1.

13. The method of claim 12, wherein the reaction is a C—C cross-coupling reaction.

14. The method of claim 13, wherein the C—C cross-coupling reaction is Selected from the group consisting of: Suzuki coupling, Heck coupling and Sonogashira coupling.

15. The method of claim 12, wherein the amount of palladium(0) complex Used in the reaction for 1 mole of substrate is 0.25 mole % or less.

16. The method of claim 12, wherein the reaction is a C—N coupling reaction.

17. The method of claim 16, wherein the reaction is a Buchwald coupling.

18. A composition comprising a palladium(0)-tris{tri-[3,5-bis (trifluoromethyl)-phenyl]-phosphine} complex of formula (I)

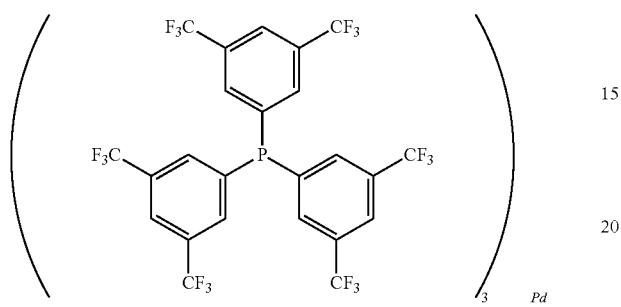

exhibiting the following properties: insolubility in water at industrially relevant temperatures: increasing solubility at room temperature in alcohols with increasing carbon atom numbers of the alcohols: and increased stability in alcohols with addition of water.

19. The palladium(0) complex of claim 18 exhibiting solubility and catalytic activity in aqueous alcohols at 110-130° C.

20. The palladium(0) complex of claim 18 having a bright yellow color.

* * * * *